(12) United States Patent
Turcott

(10) Patent No.: US 7,494,470 B1
(45) Date of Patent: Feb. 24, 2009

(54) ANALYSIS OF METABOLIC GASES BY AN IMPLANTABLE CARDIAC DEVICE FOR THE ASSESSMENT OF CARDIAC OUTPUT

(75) Inventor: Robert G. Turcott, Mountain View, CA (US)

(73) Assignee: Pacesetter Inc., Sunnyvale, CA (US)

( * ) Notice: Subject to any disclaimer, the term of this patent is extended or adjusted under 35 U.S.C. 154(b) by 472 days.

(21) Appl. No.: 10/938,173

(22) Filed: Sep. 10, 2004

(51) Int. Cl.
*A61B 5/00* (2006.01)
(52) U.S. Cl. ...................................... 600/505; 600/526
(58) Field of Classification Search ................. 600/300, 600/364, 481, 508, 526
See application file for complete search history.

(56) References Cited

U.S. PATENT DOCUMENTS

| | | | |
|---|---|---|---|
| 5,119,813 A | 6/1992 | Cohen | 128/419 D |
| 5,156,148 A | 10/1992 | Cohen | 128/419 PG |
| 5,188,106 A * | 2/1993 | Nappholz et al. | 607/24 |
| 5,241,966 A * | 9/1993 | Finkelstein et al. | 600/485 |
| 6,409,675 B1 | 6/2002 | Turcott | |
| 6,463,324 B1 * | 10/2002 | Ben-Haim et al. | 607/9 |
| 7,164,948 B2 * | 1/2007 | Struble et al. | 607/22 |
| 2003/0199956 A1 * | 10/2003 | Struble et al. | 607/122 |
| 2004/0220455 A1 * | 11/2004 | Lowe et al. | 600/300 |
| 2005/0054905 A1 * | 3/2005 | Corl et al. | 600/309 |
| 2006/0200033 A1 * | 9/2006 | Keren et al. | 600/504 |

OTHER PUBLICATIONS

Ohlsson et al., "Long term recording of cardiac output via an implantable hemodynamic monitoring device," E. Heart J. 17: 1902-1910 (1996).

* cited by examiner

*Primary Examiner*—Robert L Nasser
(74) *Attorney, Agent, or Firm*—Steven M. Mitchell

(57) ABSTRACT

Analysis of metabolic gases by an implantable medical device allows the assessment of the status of a congestive heart failure patient by providing for the assessment of cardiac output. The present invention is directed to an implanted medical device configured to measure concentrations of metabolic gases in the blood to determine cardiac output of a patient. The device is also configured to measure changes in the cardiac output of a patient. The present invention is also directed to a method of measuring cardiac output by an implanted medical device. Further, the detection of changes in cardiac output utilizing an implanted medical device as disclosed herein is useful in a method of detecting exacerbation of congestive heart failure. The implanted medical device can also be used to pace a heart to modify cardiac output in a patient.

1 Claim, 2 Drawing Sheets

ANALYSIS OF METABOLIC GASES BY AN IMPLANTABLE CARDIAC DEVICE FOR THE ASSESSMENT OF CARDIAC OUTPUT

BACKGROUND OF THE INVENTION

1. Field of the Invention

The invention relates generally to the field of implantable cardiac devices, and more particularly, to an implantable cardiac device (ICD) configured to analyze metabolic gases for the assessment of cardiac output.

2. Related Art

Many chronic diseases, such as diabetes and heart failure, require close medical management to reduce morbidity and mortality. Because the disease status evolves with time, frequent physician follow-up examinations are often necessary. At follow-up, the physician may make adjustments to the drug regimen in order to optimize therapy. This conventional approach of periodic follow-up is unsatisfactory for some diseases, such as heart failure, in which acute, life-threatening exacerbations can develop between physician follow-up examinations.

Congestive heart failure (CHF) is a chronic disease characterized by frequent exacerbations leading to expensive hospitalizations. Indeed, a patient hospitalized with CHF has a 50 percent chance of being readmitted for the same reason within 6 months. It is well known that close, routine monitoring of these patients allows early, simple, and inexpensive medical intervention which can prevent the exacerbation and eliminate the need for hospitalization. Monitoring for signs of an impending exacerbation thus both improves clinical outcomes and significantly reduces the cost of caring for these patients. It is well known among clinicians that if a developing exacerbation is recognized early, it can be easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart-failure that many patients succumb to the disease.

It is often difficult for patients to subjectively recognize a developing exacerbation, despite the presence of numerous physical signs that would allow a physician to readily detect it. This problem is well illustrated by G. Guyatt in his article entitled "A 75-Year-Old Man with Congestive Heart Failure," 1999, JAMA, 281(24): 2321-2328. Furthermore, since exacerbations typically develop over hours to days, even frequently scheduled routine follow-up with a physician cannot effectively detect most developing exacerbations. It is therefore desirable to have a system that allows the routine, frequent monitoring of patients so that an exacerbation can be recognized early in its course. With the patient and/or physician thus notified by the monitoring system of the need for medical intervention, a developing exacerbation can easily and inexpensively be terminated early in its course.

The multiplicity of feedback mechanisms that influence cardiac performance places the heart at the center of a complex control network. The neurohumoral axis includes the autonomic nervous system, consisting of sympathetic and parasympathetic branches, and numerous circulating hormones such as catacholamines, angiotensin, and aldosterone. Neural reflex arcs originating from pressure and stretch receptors, which directly measure mechanical hemodynamic status, modulate the neurohumoral axis. Similarly, chemoreceptors respond to changes in $CO_2$, pH, and $O_2$, which reflect cardiopulmonary function. The neurohumoral system influences cardiac performance at the level of the cardiac electrical system by regulating heart rate and the conduction velocity of electrical depolarizations. It also influences cardiac performance at the mechanical level, by controlling contractility, that is, the effective vigor with which the heart muscle contracts. Conventional cardiac monitors, such as defibrillators, pacemakers, Holter monitors, and cardiac event records, are tailored for the diagnosis and/or therapy of abnormalities of the cardiac electrical system. In contrast, heart failure is a disease of the cardiac mechanical system. It is primarily a failure of the myocardium to meet the mechanical pumping demands required of it. In monitoring the status of a heart failure patient, measuring the mechanical hemodynamic variables is desirable. Examples of mechanical hemodynamic variables include atrial, ventricular, and arterial pressures, and cardiac output (volume of blood pumped into the aorta per unit time).

One approach to frequent monitoring of heart failure patients that has been proposed is the daily acquisition of the patient's weight and responses to questions about subjective condition (see, for example, Alere DayLink Monitor, Alere Medical, Inc., San Francisco, Calif.). The simplicity and non-invasive aspect of this approach are desirable features. However, both the amount and the sophistication of the objective physiological data that can be acquired in this way are quite limited, which consequently limits the accuracy of the system. Furthermore, the system requires the active participation of the patient, who must not deviate from the precise data acquisition routine or risk introducing confounding factors into the acquired data.

In another approach to monitoring cardiac patients, oxygen saturation or partial pressure sensors are placed in the right ventricle for rate responsive pacing, in which the pacing rate of the pacemaker is controlled based on the metabolic demand of the body, which is a form of hemodynamic assessment and pace-parameter optimization. Assuming arterial $O_2$ is constant, a fall in venous $O_2$ below a critical level implies that the cardiac output is not sufficient to meet metabolic demand. In this case, a pacing parameter, the pacing rate, is increased.

A number of examples of a variety of measures of hemodynamic status, including both implantable embodiments (cardiac output measured using impedance plethysmography of the right ventricular volume, and right ventricular pressure) and external embodiments (cardiac output measured using Doppler ultrasound, heart sounds, blood pressure, respiratory gas analysis, and pulse oximetry) are known. External measurements of hemodynamic status are labor-intensive and can only be used during periodic follow-up examination. They are therefore not suitable for arrhythmia discrimination, dynamic pace-parameter optimization, sensitivity optimization, or capture verification.

Non-invasive techniques, such as plethysmography of vasculature, are also known. These techniques provide the basis of the conventional pulse oximeter, which by using two wavelengths of light, calculates the percent of arterial hemoglobin that is saturated with oxygen. The light is typically directed through the fingertip using a temporarily applied finger sensor. It can also be directed through other fleshy appendages such as the ear and, in infants, the foot. Optical vascular plethysmography also provides the basis for a non-invasive, continuous blood pressure monitor. A cuff containing an optical source and detector is placed over the finger. The pressure in the cuff is continuously varied so that the amount of light measured at the detector remains constant, which indicates that the volume of the vasculature is constant. In this way the arterial pressure can be inferred from the cuff pressure that is necessary to maintain constant light detection. Thus, while optical plethysmography of the vasculature is known in the art, it has to date been configured mostly for temporary, external use.

What is needed is a technique for continuously measuring cardiac output safely and accurately, with minimum disruption to a patient's normal activities.

SUMMARY OF THE INVENTION

This invention provides for analysis of metabolic gases by a pacemaker or other implantable medical device such as an implantable cardioverter defibrillator (ICD), or implanted monitor to determine cardiac output to assess the status of a congestive heart failure patient and optimize device function. Embodiments of the present invention are directed to an implanted device configured to measure concentrations of metabolic gases in the blood to determine cardiac output of a patient. The device is also configured to measure changes in the cardiac output of a patient. The present invention is also directed to a method of measuring cardiac output by an implanted device. Further, the detection of changes in cardiac output utilizing an implanted device as disclosed herein is useful in a method of detecting exacerbation of congestive heart failure. A pacemaker or ICD can also be used to pace a heart to modify cardiac output in a patient.

DETAILED DESCRIPTION OF THE INVENTION

The present invention is directed to an implantable medical device configured to obtain a measurement of blood gas concentrations, wherein the blood gas concentrations can be used to estimate cardiac output. Cardiac output can be calculated from blood gas concentrations using the Fick equation or an approximation thereof or from a calculation based on the difference in blood gas concentrations between arterial and venous blood.

Figure 1:
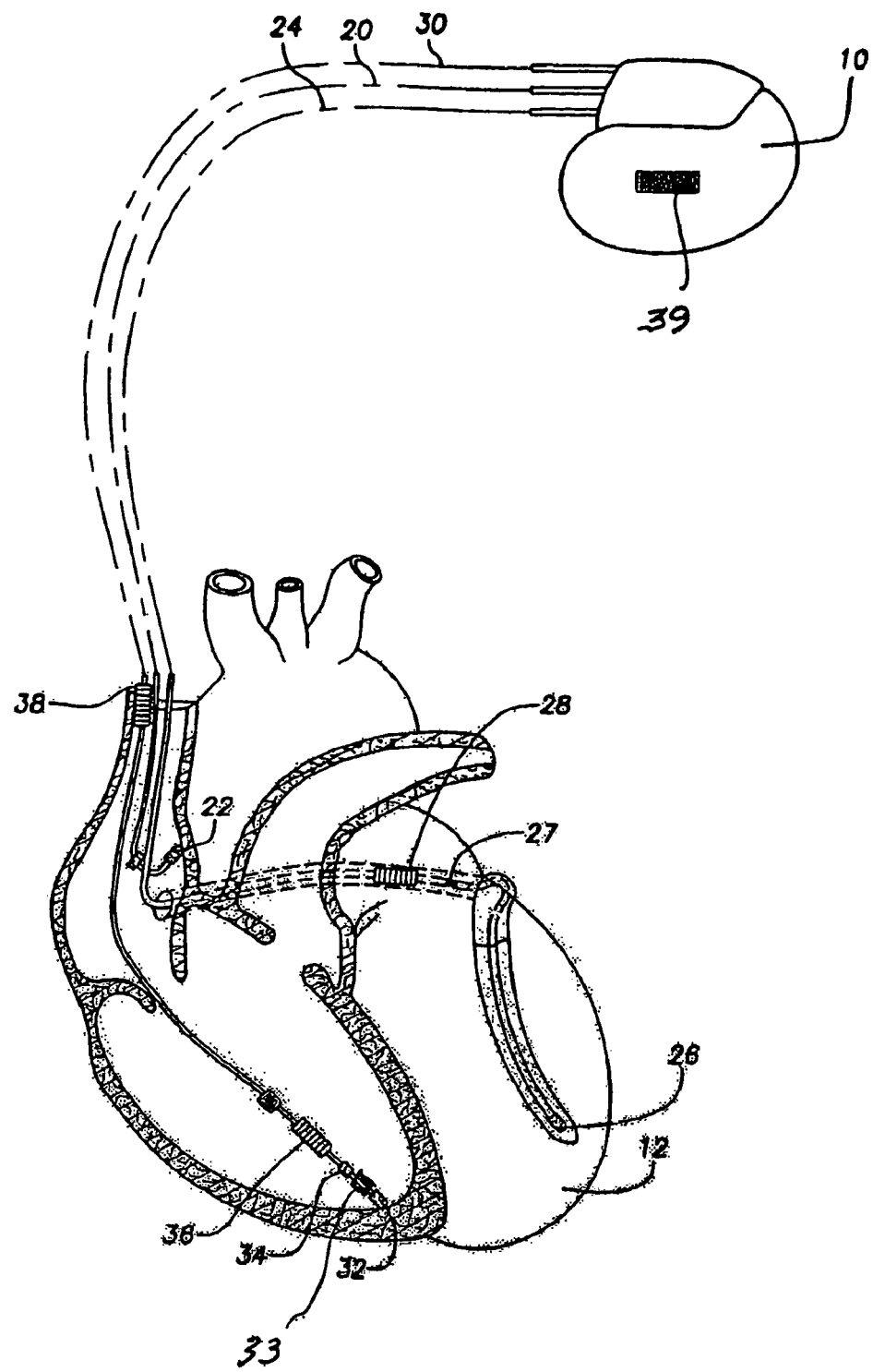
FIG. 1 is a simplified diagram illustrating an implantable stimulation device in electrical communication with at least three leads implanted into a patient's heart for delivering multi-chamber stimulation and shock therapy.

For illustration, a particular type of implanted medical device called an implantable cardioverter defibrillator (ICD) is described. A conventional ICD can deliver both pacing therapy to treat slow heart rhythms (bradyarrhythmias) and cardioversion or defibrillation therapy to treat fast heart rhythms (tachyarrhythmias). As shown in FIG. 1, an exemplary ICD 10 is in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a first, right ventricular $O_2$ sensor 33, a right ventricular ring electrode 34, a right ventricular (RV) coil electrode 36, and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Right ventricular lead 30 is capable of receiving cardiac signals and delivering stimulation in the form of pacing and shock therapy to the right ventricle. Right ventricular lead 30 is also capable of measuring venous oxygen concentration and sending that information back to an electronic circuit contained in ICD 10.

In one embodiment, a second sensor 39 is mounted extravascularly on the exterior housing of ICD 10 for measuring arterial blood gas concentration. Alternatively it is incorporated within the exterior housing or within the header. The output of sensor 39 is coupled to the electronic circuit contained in ICD 10. The electronic circuit in ICD 10 is capable of calculating a measure of cardiac output based on the difference between arterial and venous blood gas concentrations measured by sensors 33 and 39.

Except for the addition of right ventricular sensor 33 and extravascular sensor 39, ICD 10 described above is substantially the same as known ICDs, such as are described in commonly owned U.S. Pat. No. 6,658,296 B1, to Kenneth Wong, et al., issued Dec. 2, 2003, the disclosure of which is incorporated herein by reference in its entirety as though set forth in full below.

RV sensor 33 may be any of a number of well known sensors, such as a reflectance oximetry sensor of the type described, for example, in U.S. Pat. No. 4,807,629, to Michael Baudino et al., issued Feb. 28, 1989, the relevant portions of which are incorporated herein by reference as though set forth in full below. As is well known, intravascular sensor 33 may be configured to measure blood gas concentrations of mixed venous blood.

Extravascular sensor 39 for measuring arterial blood gas concentration may be an optical sensor or an electrochemical sensor. Many such sensors are well known in the art. One example of an extravascular sensor 39 is shown in commonly owned U.S. Pat. No. 6,409,675, to Robert Turcott, issued Jun. 25, 2002, the disclosure of which is incorporated herein by reference in its entirety as though set forth in full below. An improved sensor of this type is disclosed in co-pending U.S. application Ser. No. 10/764,067 filed Jan. 23, 2004, which is incorporated herein by reference. Sensor 39 may be an $O_2$ sensor. For example, the $O_2$ sensor may be a pulse oximetry sensor.

Figure 2:
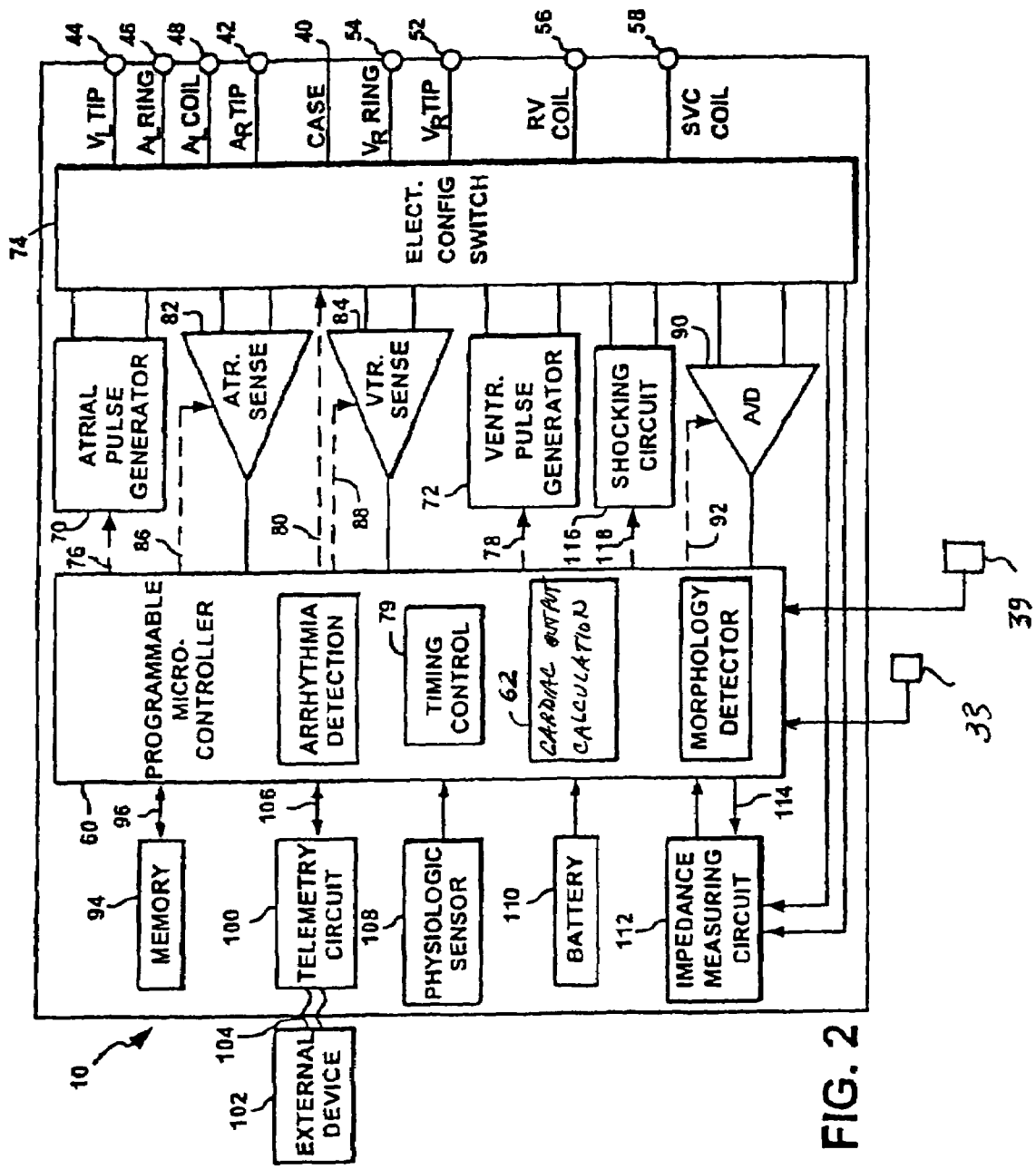
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable cardiac device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for ICD 10, shown schematically in FIG. 2, is often referred to as the "can", "case" or "case electrode" and may be programmably selected to act as the return electrode for all "unipolar" modes. Housing 40 may further be used as a return electrode alone or in combination with one or more of the coil electrodes, 28, 36 and 38, for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COWL) 56, and an SVC shocking terminal (SVC COIL) 58, which are adapted for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators, 70 and 72, are controlled by microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. The outputs of atrial and ventricular sensing circuits, 82 and 84, are connected to microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, ICD 10 utilizes atrial and ventricular sensing circuits 82 and 84 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with an external device 102, such as a programmer, transtelephonic transceiver, or a diagnostic system analyzer. The telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104. In the preferred embodiment, ICD 10 further includes a physiologic sensor 108, commonly referred to as a "rate-responsive" sensor because it is typically used to adjust pacing stimulation rate according to the exercise state of the patient. However, physiological sensor 108 may further be used to detect changes in cardiac output, changes in the physiological condition of the heart, or diurnal changes in activity (e.g., detecting sleep and wake states). Accordingly, microcontroller 60 responds by adjusting the various pacing parameters (such as rate, AV Delay, V-V Delay, etc.) at which atrial and ventricular pulse generators 70 and 72 generate stimulation pulses.

ICD 10 additionally includes a battery 110 which provides operating power to all of the circuits shown in FIG. 2. For ICD 10, which employs shocking therapy, battery 110 must be capable of operating at low current drains for long periods of time (preferably less than 10 μA), and then be capable of providing high-current pulses (for capacitor charging) when the patient requires a shock pulse (preferably, in excess of 2 A, at voltages above 2 V, for periods of 10 seconds or more). Battery 110 must also have a predictable discharge characteristic so that elective replacement time can be detected. Accordingly, ICD 10 preferably employs lithium/silver vanadium oxide batteries, as is true for most (if not all) current devices.

ICD 10 further includes a magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that external programmer 102 is in place to receive or transmit data to microcontroller 60 through telemetry circuit 100.

As further shown in FIG. 2, ICD 10 is shown as having an impedance measuring circuit 112 which is enabled by microcontroller 60 via a control signal 114.

Microcontroller 60 includes a cardiac output calculation module 62 implemented by computer executable code, firmware, and/or hardware for calculating cardiac output based on the Fick equation or on the difference in blood gas concentrations between arterial and venous blood. Microcontroller 60 receives blood gas measurement signals from sensors 33 and 39. Microcontroller 60 either processes the received measurement signals internally or stores the measurement signals and transmits them through telemetry circuit 100 to external device 102 for processing. Microcontroller 60 may be capable of calculating an absolute calibrated value of cardiac output using the Fick equation, or it may be configured to calculate an estimate or relative measure of cardiac output.

For measuring cardiac output by ICD 10, any metabolic product can be analyzed, but it is preferable that the analyte is a blood gas, such as $O_2$ or $CO_2$.

In one embodiment, telemetry circuit 100 transmits the output of the sensors, including sensors 33 and 39, to a receiver outside the body. In this embodiment, the raw data collected by ICD 10 is transmitted to a receiver prior to calculating cardiac output. Cardiac output is then calculated externally in device 102 as a function of the Fick equation.

In another embodiment, the data is processed internally by microcontroller 60 as a function of the Fick equation prior to transmitting a measure of cardiac output to a receiver outside the body.

ICD 10 may also be programmed to adjust at least one pacing parameter in response to the cardiac output. Microcontroller 60 determines whether the cardiac output requires an adjustment to cardiac pacing. If an adjustment is required, microcontroller 60 sends a signal to the appropriate stimulation electrode for pacing the heart in response to the measured cardiac output.

The Fick equation is derived below. The derivation is based on oxygen concentration, but the Fick equation is applicable to any blood gas or blood borne material:

$\Delta T$ arbitrary time interval $V_{O2}$=net amount of $O_2$ absorbed by the lungs in time $\Delta T$ (L $O_2$)

$V_{aO2}$=volume of $O_2$ carried from lungs by systemic arteries in time $\Delta T$ (L $O_2$)

$V_{vO2}$=volume of $O_2$ carried to lungs by systemic veins in time $\Delta T$ (L $O_2$)

$C_{aO2}$=concentration of $O_2$ in systemic arterial blood (L $O_2$/L blood)

$C_{vO2}$=concentration of $O_2$ in systemic venous blood (L $O_2$/L blood)

$V_{blood}$=volume of blood carried from or to the lungs in time $\Delta T$ (L blood)

$V_{O2}$=rate at which $O_2$ is consumed by or delivered to the body (L $O_2$/min)

CO=cardiac output (L blood/min)

$S_{aO2}$=arterial $O_2$ saturation: fraction of arterial hemoglobin that is loaded with $O_2$ $S_{vO2}$=venous $O_2$ saturation: fraction of venous hemoglobin that is loaded with $O_2$

[Hb]=concentration of hemoglobin (g/dL blood)

1.34=conversion factor relating [Hb] concentration to $O_2$ volume, assuming fully saturated hemoglobin (mL O2/g Hb)

Consider the consumption of oxygen by the body as seen at the level of the lungs. In time $\Delta T$, a net volume $V_{O2}$ is inspired by the lungs, which in the steady state is equal to the net amount consumed by the body. A volume $V_{aO2}$ is delivered to systemic arterial circulation, and a volume $V_{vO2}$ is returned on the venous side.

$$V_{O2} = V_{aO2} - V_{vO2} \quad (1)$$

Expressing the gas volume carried in the blood in terms of their concentrations yields:

$$V_{aO2} = C_{aO2} \cdot V_{blood}, \atop V_{vO2} = C_{vO2} \cdot V_{blood}} \quad (2)$$

where $V_{blood}$ is the volume of blood that passes a given point in time $\Delta T$. Since the cardiac output CO is by definition, CO≡stroke volume·heart rate=$V_{blood}/\Delta T$ (with equality holding if there is no valvular regurgitation or intracardiac shunt), substituting (2) into (1) and dividing by $\Delta T$ gives;

$$V_{O2} = \{C_{aO2} - C_{vO2}\} \cdot V_{blood}$$

$$V_{O2}/\Delta T \equiv \dot{V}_{O2} = \{C_{aO2} - C_{vO2}\} \cdot V_{blood}/\Delta T, \quad (3)$$

$$\dot{V}_{O2} = \{C_{aO2} - C_{vO2}\} \cdot CO$$

or, $$CO = \dot{V}_{O2}/\{C_{aO2} - C_{vO2}\} \quad (4)$$

This last result, Eq. (4), is the Fick equation. It can be expressed in terms of oxygen saturation, that is, the percentage of hemoglobin that is loaded with oxygen, using the relation $C_{aO2}$=(1.34 mL/gHb)·[Hb gHb/dL]·$S_aO2$·(10 dL/L)·(L/1000 mL)=0.0134·[Hb]·$S_aO2$ for arterial $O_2$ saturation and a similar relation for venous O2 saturation. Eq. (4) thus becomes $$CO = \dot{V}_{O2}/\{0.0134 \cdot [Hb] \cdot (S_aO2 - S_vO2)\} \quad (5)$$

and is expressed in units of L/min.

Other gases or products of metabolism, e.g., $CO_2$, can be used in place of $O_2$. Because most oxygen in the blood is bound to hemoglobin, the Fick equation can be expressed in terms of $O_2$ saturation and hemoglobin concentration, as shown above. Thus, the Fick equation can be expressed more generally as $$CO = k/\{C_a - C_v\}.$$

Where k is a constant which approximates consumption of the blood gas, $C_a$ is a measure of arterial blood gas content and $C_v$ is a measure of venous blood gas content. Alternatively, the equation can be expressed in terms of hemoglobin saturation ($S_a$ for arterial hemoglobin saturation and $S_v$ for venous hemoglobin saturation) as:

$$CO = k/\{S_a - S_v\},$$

where k is a constant that approximates consumption or production of a blood gas bound to hemoglobin. This is advantageous because it allows cardiac output to be estimated using oxygen saturation sensors. The derivation assumes steady state. Following an acute change in the system, the Fick equation is not valid until steady state has returned, which may require seconds to tens of seconds, or even longer.

ICD 10 or other implantable medical device can be configured to work in conjunction with external equipment or a monitor that measures $\dot{V}_{O2}$. Thus, ICD 10 or other device can be configured to obtain an absolute calibrated value of cardiac output using the Fick equation. However, it is preferable that ICD 10 functions independently in assessing cardiac output in such a way that external equipment, patient compliance and need for physician interaction is minimized.

In certain embodiments, ICD 10 can utilize the relative difference in oxygen saturation between the arterial and venous blood gas concentrations to determine cardiac output. This is mathematically equivalent to the use of the Fick equation to calculate cardiac output although one advantage is that it is not necessary to measure net inspired $O_2$ or expired $CO_2$ as required by the Fick equation, represented as $\dot{V}_{O2}$ in Eqs. (4) and (5). The Fick equation relates cardiac output, consumption or production of a substance, and differences between arterial and venous concentrations of the substance. It assumes steady state conditions. When the substance is a metabolic gas, the equation requires knowledge of net inspired $O_2$ or expired $CO_2$. However, an ICD or other device could approximate the measure of inspired gas, or treat it as a constant in certain situations. For example, when the patient is at rest the baseline metabolic rate can be approximated based on the patient's size. This allows a good estimate of cardiac output using Fick equation (4) or (5) and replacing measured $\dot{V}_{O2}$ with an approximation. Thus, the cardiac output measurement provided by the ICD or other device need not incorporate measured inspired $O_2$ or expired $CO_2$. Rather, an approximation of net inspired $O_2$ or expired $CO_2$ is used. It should be clear to those of skill in this field that the term can be an absolute measure or it can be a constant value or an approximation when appropriate. The device can therefore provide a measurement of cardiac output that is an estimate of cardiac output. Such a measurement is useful in itself, and can also be used to track changes in relative cardiac output that signal the status of the CHF patient.

Another simplification of the implementation of Eqs. (4) and (5) involves the recognition that, in the absence of lung pathology, $S_aO2$ is nearly always 100% or close to 100%. Thus, in some embodiments $S_aO2$ is assumed to be constant and data from the extravascular sensor 39 is not used, or alternatively, the extravascular sensor is not included in ICD 10 or similar implanted device.

Cardiac output derived by application of the Fick equation in an implantable system can be used to automatically optimize the operating parameters of the system. For example, if the system comprises a pacemaker, then measurements of cardiac output can be used to optimize the atrio-ventricular (AV) pacing interval, also known as the AV delay (AVD), by selecting as the optimum and then using the AVD which produces the greatest cardiac output. In a specific embodiment the pacemaker delivers one test AVD for 2-5 minutes, records the cardiac output, then changes to another test AVD and repeats the process. Each of a set of test AVDs is used in random order. After the cardiac output has been recorded for each test AVD, the pacemaker selects the test AVD which produced the greatest cardiac output as the optimum and then paces with it continuously. Alternatively, the device can perform a numerical analysis using the set of recorded cardiac outputs in order to interpolate the optimum AVD from the data. In one specific example, it calculates the parameters of the best-fitting $3^{rd}$ degree polynomial, and takes the location of the maximum of the polynomial as the optimum AVD. A similar optimization technique can be performed for the interventricular pacing intervals in biventricular pacemakers, or in general, for any set of pacing intervals.

In the application of cardiac output to the optimization of pacing intervals, obtaining the absolute calibrated value of cardiac output is not necessary. In other words, it is not necessary to measure $\dot{V}_{O2}$. An absolute calibrated value of cardiac output is not required because a measure of cardiac output that allows a relative comparison of the efficacy of different pacing intervals is sufficient. Because of this, rather than calculating a numerical value of cardiac output, as given in the Fick equation, it is sufficient to simply note the difference in arterial and venous blood concentrations. For example, if the Fick equation is implemented using oxygen saturation, it is the difference in oxygen saturation between arterial and mixed venous blood that is most relevant, not the calibrated value of cardiac output. Since the difference appears in the denominator of the Fick equation, smaller differences are associated with larger cardiac outputs. Thus, the ICD would record the $O_2$ saturation difference associated with each pacing interval and select as the optimum pacing interval the one which minimizes the $O_2$ saturation difference. This is computationally less intensive than calculating a true cardiac output, and avoids the need for a proportionality constant, as well as the computation of a division operation. Nevertheless, it is equivalent to performing optimization based on cardiac output derived from the Fick equation.

The present invention is also directed to a method of measuring cardiac output using an ICD or other implanted medical device. The method comprises receiving an arterial blood gas concentration measurement; receiving a venous blood gas concentration measurement; and using the arterial and venous blood gas concentration measurements to determine a measure of cardiac output. In this aspect of the present invention, receiving an arterial blood gas concentration measurement comprises receiving an arterial blood gas measurement from extravascular sensor 39 proximate to ICD 10. Receiving a venous blood gas concentration measurement comprises receiving a blood gas concentration measurement in mixed venous blood. Such a measurement comprises receiving a blood gas concentration measurement from sensor 33 placed in the right ventricle of the heart. As noted above, the blood gas concentration measured is at least one of $O_2$ and $CO_2$ and includes saturation measurements as well as strict concentration measurements.

In the present method, the data from the blood gas concentration measurements or blood gas saturation measurements is calculated to yield a measure of cardiac output based on the difference in oxygen saturation between the arterial and venous blood gas concentrations.

The present invention is also directed to a method of detecting relative changes in cardiac output using an ICD or other implantable medical device. In this aspect, the method of comprises receiving an arterial blood gas concentration measurement; receiving a venous blood gas concentration measurement; and using the arterial and venous blood gas concentration measurements to determine a measure of cardiac output. The device is further configured to detect relative changes in cardiac output. Microcontroller 60 calculates cardiac output based on the relative difference in blood gas concentrations, such that over a predetermined time interval the device is capable of detecting changes in cardiac output.

The present invention is also directed to a method of detecting exacerbation of CHF. In this embodiment, ICD 10 can be further configured to detect an impending exacerbation based on the changes detected in cardiac output. ICD 10 or other implantable device can be programmed to detect the changes in cardiac output that signal an impending exacerbation. Such changes are well known in the art.

The present invention is also directed to a method of pacing a heart to modify cardiac output using an ICD. This method comprises receiving an arterial blood gas concentration measurement; receiving a venous blood gas concentration measurement; calculating a measure of cardiac output using the arterial and venous blood gas concentration measurements; determining a pacing interval to modify cardiac output; and delivering an electrical pacing to the heart through a stimulation electrode. Such pacing can be used to optimize AV or interventricular pacing intervals wherein the cardiac output of the heart is increased by about 10 percent. This method can be used to pace the heart to prevent or ameliorate exacerbation of CHF.

Having now fully described this invention, it will be understood by those of skill in the art that the same can be performed within a wide and equivalent range of conditions, formulations, and other parameters without affecting the scope of the invention or any embodiment thereof.

What is claimed is:

1. An implantable cardiac device comprising:
   an extravascular sensor for measuring arterial blood gas content;
   an intravascular sensor for measuring venous blood gas content; and
   an electronic circuit for providing an indication of cardiac output based on the difference between said arterial and venous blood gas contents wherein said extravascular sensor is incorporated on a surface of a header of an exterior housing of the electronic circuit.

* * * * *